United States Patent [19]

Kuntz et al.

[11] Patent Number: 4,872,465
[45] Date of Patent: Oct. 10, 1989

[54] LIGHT-WEIGHT DISPOSABLE PROTECTIVE FACE SHIELD

[76] Inventors: David H. Kuntz, 11810 Bel Ter., Los Angeles, Calif. 90049; Louis F. Muller, 919 Main St., El Segundo, Calif. 90245

[21] Appl. No.: 281,743

[22] Filed: Dec. 9, 1988

Related U.S. Application Data

[63] Continuation-in-part of Ser. No. 138,070, Dec. 28, 1987, Pat. No. 4,825,878.

[51] Int. Cl.$^4$ ............................................. A61F 9/04
[52] U.S. Cl. .................................. 128/857; 128/858; 128/207.11; 2/9
[58] Field of Search ............... 128/857, 858, 859, 863, 128/206.12, 206.21, 206.23, 204.24, 207.11, 201.22, 201.23; 2/9, 12, 173, 206

[56] References Cited

U.S. PATENT DOCUMENTS

| | | | |
|---|---|---|---|
| 1,523,884 | 1/1925 | Leduc | 128/863 |
| 2,294,593 | 9/1942 | Bailey | 128/857 |
| 2,631,287 | 3/1953 | Malcolm, Jr. | 2/9 |
| 2,665,686 | 1/1954 | Wood et al. | 128/206.12 |
| 4,386,277 | 5/1983 | Forshee | 2/9 X |
| 4,589,408 | 5/1986 | Singer | 128/132 R |
| 4,594,999 | 6/1986 | Nesbitt | 128/134 X |
| 4,619,254 | 10/1986 | Moretti et al. | 128/201.23 |
| 4,621,378 | 11/1986 | Hatchman | 2/12 X |
| 4,665,566 | 5/1987 | Garrow | 128/201.22 X |

Primary Examiner—Robert A. Hafer
Assistant Examiner—Kevin G. Rooney
Attorney, Agent, or Firm—Philip D. Junkins

[57] ABSTRACT

A light-weight, disposable face shield assembly for the protection of the eyes and face of a wearer from accidental exposure to infections, hazardous or undesirable substances. The shield assembly includes an elongated, generally rectangular, semi-flexible, transparent face protection panel having a central panel section and like side panel sections which are foldable rearwardly with respect to the central panel section and a semi-flexible head support strip for the face protection panel in alignment with the upper portion of such panel. The head support strip has its ends affixed to the ends of the face protection panel and is of a length that is less than the length of such panel. The head support strip also includes a central strip portion and like side strip portions which are foldable rearwardly with respect to the central strip portion with the fold lines of the head support strip lying within the fold lines of the face protection panel. An elastic head band is affixed to the ends of the head support strip for maintaining such strip in position about the forehead of a wearer of the face shield assembly whereby the face protection panel is formed up into rigidly-supported, arcuate spaced protection orientation about the face of a wearer.

10 Claims, 2 Drawing Sheets

LIGHT-WEIGHT DISPOSABLE PROTECTIVE FACE SHIELD

RELATED APPLICATION

This is a continuation-in-part of application Ser. No. 138,070, filed Dec. 28, 1987 now U.S. Pat. No. 4,825,878 issued 5/2/89.

BACKGROUND OF THE INVENTION

The present invention relates to face shields for the protection of the eyes and face of wearers from accidental exposure to infections, hazardous and undesirable substances. More particularly, the invention relates to anti-infection shields for the protection of health care workers and professionals and laboratory personnel from accidental exposure to infectious and/or hazardous fluids and particulate materials.

Health care workers have long recognized that caring for patients with certain infectious diseases poses risks of contracting such diseases. For example, many cases have been reported of accidental transmission of Hepatitis B from patients to persons involved in their care. More recently, the life threatening epidemic of Acquired Immunodeficiency Syndrome (AIDS) caused by the Human Immunodeficiency Virus (HIV) has aroused great concern. Although the bulk of cases of patient to health care worker cross infection have resulted from accidental needlesticks, medical office, hospital, surgical, dental and laboratory personnel are now required to use extreme care in the handling of all patients and body fluids as potentially infected with HIV and other pathogens. Particular attention has been directed to the risk to surgeons and operating room personnel of infection through splashing or splattering of blood or other body fluids onto open wounds, into mouths or into the eyes of such personnel during the performance of surgical procedures.

In the United States, the centers for Disease Control, Public Health Service of the U. S. Department of Health and Human Services, has issued a comprehensive series of recommendations for the prevention of HIV transmission in health care settings and such recommendations are applicable to the risks of exposure to all infected body fluids. These recommendations show an increasing concern for protection of the eyes (particularly conjunctiva) if aerosolization or splashing of blood or other fluids is likely to occur. Thus, according to the Centers for Disease Control, eye shields should be worn by medical personnel and laboratory workers to prevent blood and other body fluids from splattering into the eyes. An effective eye shield must protect the eyes no matter which direction the wearer faces. Ordinary eyeglasses are not sufficient protection.

It is an object of the present invention to provide a face shield for the protection of the eyes and face of wearers from accidental exposure to infectious, hazardous and undesirable substances.

It is another object of the invention to provide a face shield for the protection of health care workers and professionals and laboratoy personnel from accidental exposure to body fluids from infected patients.

It is a further object of the invention to provide a low cost, disposable face shield for health care workers and professionals and laboratory personnel subject to accidental exposure to infectious body fluids.

Another object of the invention is to provide a light-weight, full-face shield for the protection of the eyes and face of health care and laboratory personnel from spattered blood and other body fluids containing infectious disease forms.

Yet another object of the invention is to provide a light-weight, protective face shield for a wide variety of worker-wearers exposed to infectious, hazardous and undesirable substances.

Still another object of the invention is to provide a light-weight, disposable protective face shield which is readily formed up from a flat packaged form and may be worn over ordinary eyeglasses.

Other objects and advantages of the invention will become apparent from the following summary and detailed description of preferred embodiments of the invention taken in conjunction with the accompanying drawing figures.

SUMMARY OF THE INVENTION

The present invention relates to light-weight, disposable, face shields for the protection of the eyes and face of wearers from accidental exposure to infectious, hazardous and undesirable substances. It is of particular interest in the protection of health care workers and professionals and laboratory personnel from accidental exposure to body fluids from infected patients. The shield includes: a semi-flexible transparent eye/face protection panel; and a semi-flexible head support strip for the protection panel. An elastic head band is affixed to the head support strip for holding same to the forehead of a wearer with the result that the protection panel forms up in an arcuate outwardly spaced fashion about the wearer's head to provide full face protection while allowing total peripheral vision by the wearer.

The transparent eye/face protection panel may be provided with a frame structure of semi-flexible sheet plastic material or coated paper board including an elongated upper horizontal frame portion with depending side or leg portions. The frame structure may be affixed to the front or rear side of the semi-flexible eye/face protection panel which is formed of relatively thin optically clear polyester sheet material or other appropriate clear plastic sheet material. The clear eye/face protection panel also may be coated with an anti-glare substance (compatible with the panel material) where the face shield is to be worn under high lighting conditions. The frame structure of the face shield may be comprised of one or more substantially like sheets of plastic or paper board with one of the frame sheets affixed to the front side and the other of the sheets (if utilized) affixed to the rear side of the eye/face protection panel.

In its unformed orientation (for flat packaging and/or storage) the end portions of the eye/face protection panel are folded inwardly over the central portion of the panel in overlapping fashion. The head support strip (affixed at its ends to the rear side of the protection panel at its upper corner areas) is of somewhat shorter length than the upper horizontal portion of the protection panel and has its end portions also folded inwardly over its central portion in overlapping fashion within the folded protection panel. The resulting folded face shield has an area of approximately 50% of the area of the unfolded protection panel and is most suitable for flat packaging and storage. The elastic head band for the face shield has its ends affixed to the upper corner areas of the protection panel at the points of affixation of the head support strip to the protection panel. Instead of an elastic head band, the face shield may be provided with head ties to maintain the shield in place on the wearer's head.

BRIEF DESCRIPTION OF THE DRAWING FIGURES

DETAILED DESCRIPTION OF THE PREFERRED EMBODIMENTS

Figures 1, 1A:
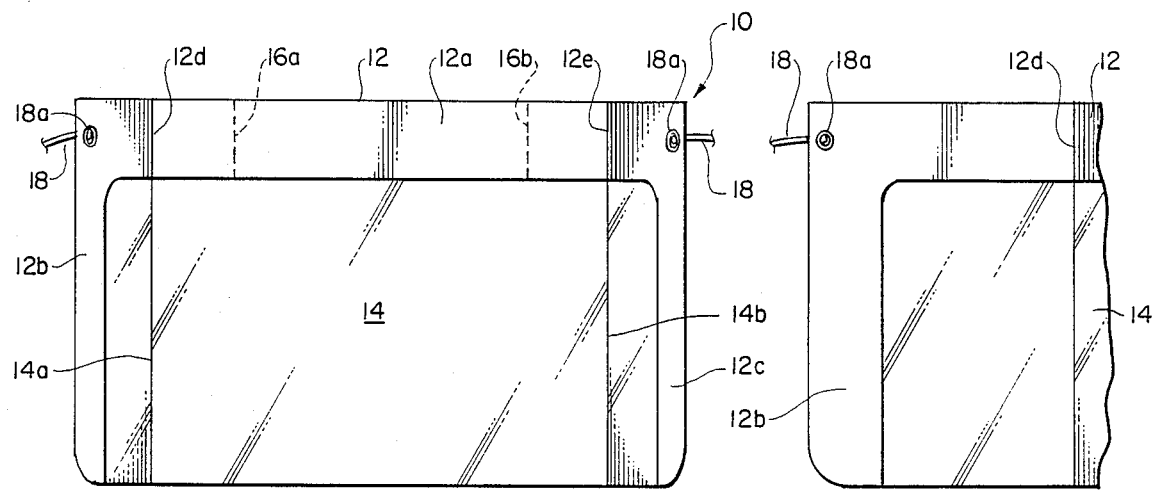
FIG. 1 is a front view of a first form of the eye/face shield of the invention with the shield in its partially formed orientation with end portions of the transparent protective panel folded rearwardly before applying the shield to a wearer's head.
FIG. 1a is a partial side view of the eye/face shield of FIG. 1 showing particularly one of the end portions of the transparent protection panel.
Figure 2:
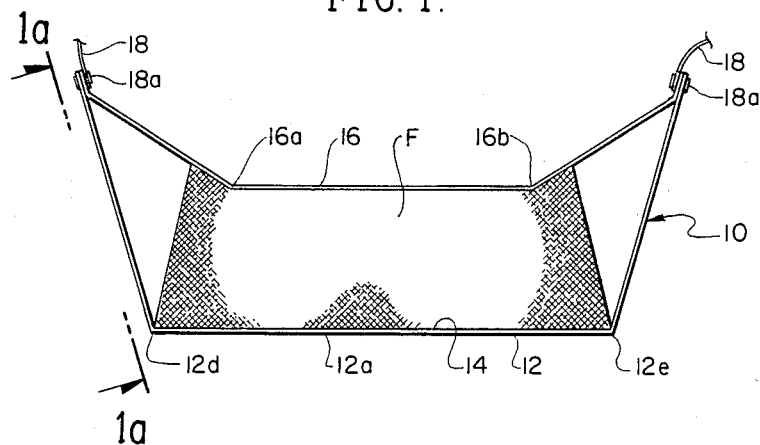
FIG. 2 is a top view of the eye/face shield of FIG. 1.
Figure 3:
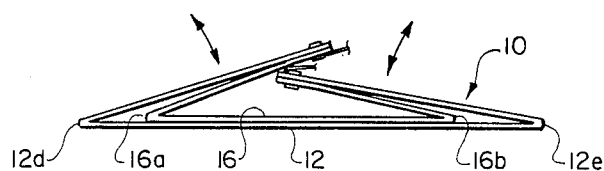
FIG. 3 is a top view of the eye/face shield of FIGS. 1 and 2 with end portions of the transparent protection panel and inner head support strip folded inwardly in overlapping fashion to nearly a fully collapsed position for packaging.

Referring initially to FIGS. 1 and 2 of the drawings there is illustrated front and top views, respectively, of a first preferred form of the eye/face shield 10 of the invention in its open (unpackaged) form immediately prior to the mounting of the shield assembly to a wearer's head. The shield includes as its principal elements: a semi-flexible frame structure 12 supporting an elongated, generally-rectangular, transparent eye/face protection panel 14; and a semi-flexible head support strip 16 with an elastic head band 18 affixed to the ends of the head support strip at the point of affixation of the ends of strip 16 to the upper corner areas of the frame structure 12. The frame structure 12 of the eye/face shield 10 preferably is formed of semi-flexible sheet plastic material, or semi-flexible coated paper board, and includes an elongated upper horizontal frame portion 12a with depending side or leg portions 12b and 12c. The frame structure 12 may be comprised of a single sheet of plastic or paper board material affixed to the front or rear side of the transparent protection panel 14 or the frame structure may be comprised of sheets of the plastic or paper board material affixed to both sides of panel 14 along the upper horizontal portion of the panel and along the vertical side portions of the panel. It will be noted from FIGS. 1 and 1a that vertical score lines 12d and 12e are provided across the upper horizontal frame structure portion 12a and from FIG. 2 that such score lines result in partial folding of the frame structure 12 at such score (fold) lines. The score (fold) lines 12d and 12e extend vertically downward and across the transparent protection panel 14 as fold lines 14a and 14b, respectively.

Figure 4:
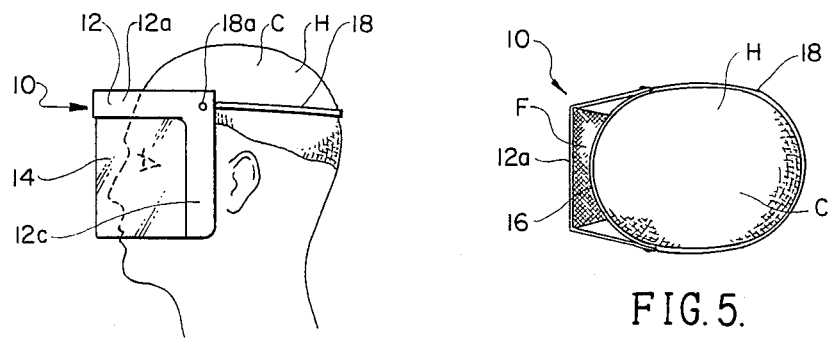
FIG. 4 is a side view of the eye/face shield of FIGS. 1 and 2 of the invention in operative protective position mounted on the head of a wearer of the shield.

From FIG. 2 it will be noted that the semi-flexible head support strip 16 is somewhat shorter in length than the upper horizontal frame portion 12a of the frame structure 12. As shown in FIGS. 1 and 2 the head support strip 16 is affixed at its ends to the upper corners of frame structure 12 by rivet means 18a which also affix the ends of elastic head band 18 to the frame structure 12. The head support strip 16 may be formed of semi-flexible sheet plastic material, or semi-flexible coated paper board, and also may be provided with an absorptive liner or facing layer (not illustrated) of cloth, soft foam plastic material or absorptive paper for absorbing forehead moisture as may be generated by the wearer during use of the shield. The head support strip 16 also includes vertical score (fold) lines 16a and 16b for assisting in shaping and fitting the shield 10 to the wearer's head. Since the head support strip 16 is of shorter overall length than the upper horizontal frame portion 12a (to which it is attached) and the fold lines 16a and 16b of strip 16 lie within the fold lines 12d and 12e of the frame portion 12a, the head support strip 16 (when applied to the wearer's head H as shown in FIGS. 4 and 5) firmly supports transparent protection panel 14 of the eye/face shield 10 in proper arcuate spaced and full protective alignment with the wearer's head without adversely affecting the wearer's forward and peripheral vision.

Figure 5:
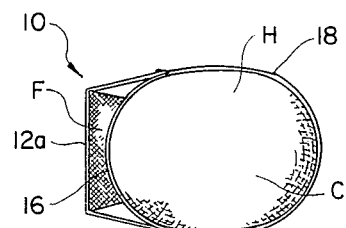
FIG. 5 is a top view of the eye/face shield of FIGS. 1 and 2 of the invention in operative protective position mounted on the head of the wearer.

The eye/shield 10 of FIGS. 1 and 2 may be provided with a flexible, fluid resistant fabric material piece F extending between the central section of the upper horizontal frame portion 12a and the central section of the head support strip 16 for providing added protection to the wearer of the shield 10 from the splattering of body fluids that may be virus infected (also see FIG. 5). The fabric piece F also stabilizes the central positioning of the transparent protective panel 14 with respect to the head support strip 16 so that the panel 14 rests symmetrically with respect to the wearer's head. The face shield assembly 10 may be provided with pressure sensitive adhesive means, Velcro type fasteners or other type fastener means along the inner surface of the head support strip for attachment of the assembly to the lower front edge of a surgical cap C that may be worn by the wearer of the face shield as shown in FIGS. 4 and 5. It should also be understood that the ends of the head support strip 16 and the ends of the elastic head band 18 may be affixed to the upper corners of the frame structure by means other than the rivet fastener means 18a as shown in FIGS. 1 and 2.

In FIG. 5 the eye/face shield assembly 10 of FIGS. 1 and 2 is shown collapsed nearly to its pre-use, flat-packaged and/or shield storage form with the shorter head support strip 16 folded within the folded frame structure 12 bearing the folded protection panel. With the shield assembly fully collapsed (end portions fully folded inwardly over its central portion in overlapping fashion, the resulting folded face shield has an area of approximately 50% of the area of the unfolded protection panel.

Figure 6:
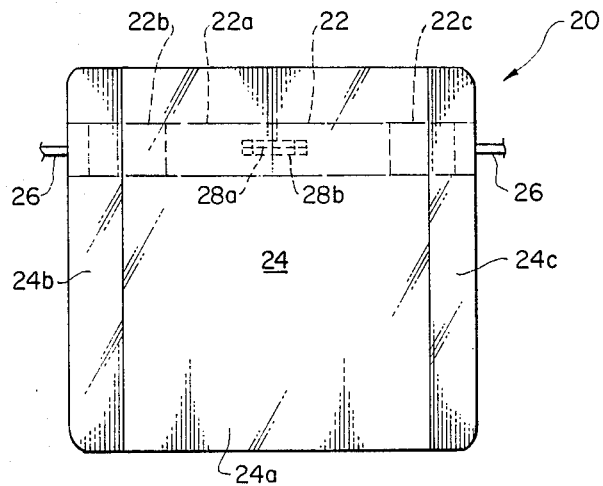
FIG. 6 is a front view of another form of the eye/face shield of the invention with the shield in its partially formed orientation with the end portions of the transparent protection panel folded rearwardly before applying the shield to a wearer's head.
Figure 7:
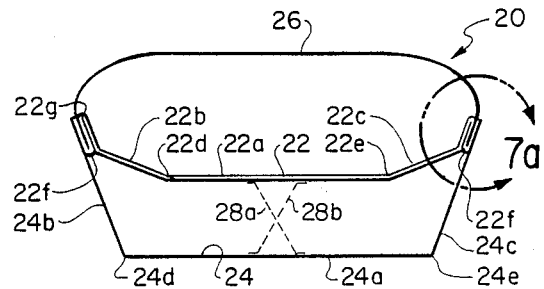
FIG. 7 is a top view of the eye/face shield of FIG. 6.

In FIGS. 6 and 7 of the drawings there is illustrated front and top views, respectively, of another preferred form of the eye/face shield of the invention in its open (unpackaged) form immediately prior to the mounting of the shield to a wearer's head. The shield 20 includes as its principal elements: a semi-flexible, transparent eye/face protection panel 24 of generally rectangular configuration (without any frame structure); and a semi-flexible head support strip 22 with an elastic head band 26 affixed to the ends of the head support strip at the point of affixation of the ends of strip 22 to the upper corner areas of the protection panel 24. It will be noted that vertical score lines 24d and 24e are provided across the protection panel 24 and divide such panel into a central panel section 24a and side panel sections 24b and 24c which are foldable at such score (fold) lines inwardly and rearwardly.

Figure 7A:
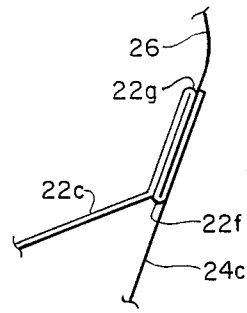
FIG. 7a is an enlarged partial top view of the eye/face shield of FIG. 7 showing the protection panel to head support strip and elastic head band connection system.
Figure 9:
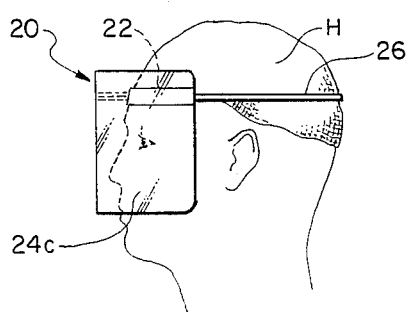
FIG. 9 is a side view of the eye/face shield of FIGS. 6 and 7 of the invention in operative protective position mounted on the head of a wearer of the shield.
Figure 10:
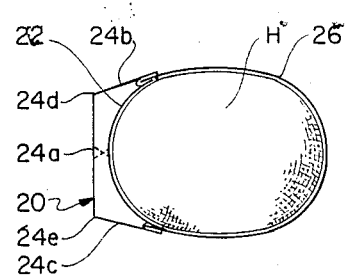
FIG. 10 is a top view of the eye/face shield of FIGS. 6 and 7 of the invention in operative protective position mounted on the head of the wearer.

From FIG. 7 it will be noted that the semi-flexible head support strip 22 is somewhat shorter in length than the protection panel 24 (panel sections 24a, 24b and 24c). Also, as shown in FIGS. 7 and 7a the head support strip 22 is affixed to the upper corners of the protection panel 24 by double folds 22f and 22g at each end of strip 22 with such folds being adhesively cemented to one-another and cemented to panel 24. The ends of the elastic head band 26 extend into the fold system 22f and 22g and are thereby also affixed to the shield assembly 20. The head support strip 22 may be formed of semi-flexible sheet plastic material, or semi-flexible coated paper board, and also may be provided with an absorptive liner or facing material for absorbing forehead moisture. The head support strip 22 also includes vertical score (fold) lines 22d and 22e dividing such strip into a central strip section 22a and side strip sections 22b and 22c for assisting in shaping and fitting the shield 20 to the wearer's head. Since the head support strip 22 is of shorter overall length than the upper horizontal portion of protection panel 24 and the fold lines 22d and 22e of strip 22 lie within the fold lines 24d and 24e of the protection panel 24, the head support strip 22 (when applied to the wearer's head H as shown in FIGS. 9 and 10) firmly supports transparent protection panel 24 of the eye/face shield 20 in proper arcuate spaced and full protection alignment with the wearer's head without adversely affecting the wearer's forward and peripheral vision. It should be understood that the ends of the head support strip 22 may be affixed to the upper corners of the protection panel by means other than the adhesive means described above.

As shown in FIGS. 6 and 7, the eye/face shield assembly 20 may be provided with a pair of flexible straps 28a and 28b (shown as dashed lines) which cross each other and extend between the top central edge portion of the protection panel (central panel section 24a) and the central section 22a of the head support strip 22. The ends of such straps may be affixed to the protection panel and the head support strip by any suitable means. These straps stabilize the central positioning of the transparent protective panel 24 with respect to the head support strip 22 so that the panel 24 rests symmetrically with respect to the wearer' head.

Figure 8:
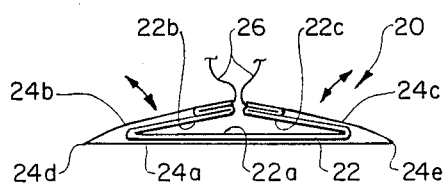
FIG. 8 is a top view of the eye/face shield of FIGS. 6 and 7 with end portions of the transparent protection panel and inner head support strip folded inwardly in overlapping fashion to nearly a fully collapsed position for packaging.

In FIG. 8 the eye/face shield assembly 20 of FIGS. 6 and 7 is shown collapsed nearly to its pre-use, flat-packaged and/or shield storage form with the shorter head support strip 22 folded within the folded transparent protection panel 24. With the shield assembly 20 fully collapsed (end portions fully folded inwardly over its central portion in overlapping fashion, the resulting folded face shield has an area of approximately 50% of the area of the unfolded protection panel.

In the specification and drawing figures there has been set forth preferred embodiments of a light-weight, disposable, anti-infection face shield for the protection of health care workers and professionals and laboratory personnel from accidental exposure to body fluids from virus infected individuals and from accidental exposure to other hazardous liquids or particulate materials, in accordance with the invention. Although specific terms have been employed in describing the invention, they are used in a generic and descriptive sense only and not for purposes of limitation, the scope of the invention being defined in the following claims.

What is claimed is:

1. A light-weight, disposable face shield assembly for the protection of the eyes and face of a wearer from accidental exposure to infectious, hazardous or undesirable substances, said face shield assembly comprising:
    (a) an elongated, generally rectangular, semi-flexible, transparent face protection panel including a central panel section and like side panel sections foldable rearwardly along vertical fold lines with respect to the central panel section;
    (b) an elongated, semi-flexible head support strip for said face protection panel in alignment with the upper portion of said panel and having a length that is less than the length of said face protection panel, said head support strip including a central strip portion and like side strip portions foldable rearwardly along vertical fold lines with respect to the central strip portion with the fold lines of said head support strip lying within the fold lines of said face protection panel;
    (c) means for attaching the ends of said head support strip to the ends of said face protection panel in its upper portion whereby said panel is supported in spaced orientation from said head support strip; and
    (d) means attached to said head support strip at the ends thereof for maintaining said strip in position about the forehead of a wearer of said face shield assembly whereby said face protection panel is formed up into rigidly-supported arcuate spaced protection orientation about the face of a wearer.

2. A light-weight, disposable face shield assembly as claimed in claim 1 wherein said transparent face protection panel is provided with a semi-flexible supporting frame member including an upper horizontal frame portion and downwardly depending side portions affixed to said face protection panel, said upper horizontal frame portion including fold lines corresponding to the fold lines of said panel.

3. A light-weight, disposable face shield assembly as claimed in claim 2 wherein said frame member is formed of a front sheet of semi-flexible material affixed to said transparent face protection panel at its peripheral edge.

4. A light-weight, disposable face shield assembly as claimed in claim 2 wherein said frame member is formed of a rear sheet of semi-flexible material affixed to said transparent face protection panel at its peripheral edge.

5. A light-weight, disposable face shield assembly as claimed in claim 2 wherein said frame member is formed of front and rear sheets of semi-flexible material affixed to and sandwiching said transparent face protection panel at its peripheral edge.

6. A light-weight, disposable face shield assembly as claimed in claim 1 wherein the means attached to said head support strip at the ends thereof for maintaining said strip in position about the forehead of a wearer comprises an elastic head band with its ends attached to the ends of said head support strip at the points at which the ends of said head support strip are attached to the ends of said face protection panel.

7. A light-weight, disposable face shield assembly as claimed in claim 1 wherein the means attached to said head support strip at the ends thereof for maintaining said strip in position about the forehead of a wearer comprises a pair of tie strings with their ends attached to the ends of said head support strip at the points at which the ends of said head support strip are attached to the ends of said face protection panel.

8. A light-weight, disposable face shield assembly as claimed in claim 1 wherein the elongated, generally rectangular, semi-flexible, transparent face protection panel of said face shield assembly is formed of optically clear sheet material selected from the group consisting of an acetate plastic or a polyester plastic.

9. A light-weight, disposable face shield assembly as claimed in claim 1 wherein said head support strip, with its ends attached to the ends of said face protection panel in the upper portion thereof, is of a length in its central strip portion and side strip portions such that it is foldable within said face protection panel when the side panel sections thereof are folded in overlapping fashion whereby said face shield assembly is compactable to a flat orientation for packaging.

10. A light-weight, disposable face shield assembly as claimed in claim 1 wherein means are provided between the top of the central panel section of said face protection panel and the central strip portion of said head support strip to stabilize the central positioning of said face protection panel with respect to said head support strip whereby said panel is positioned symmetrically with respect to the wearer's head.

* * * * *